US008475533B1

(12) United States Patent  (10) Patent No.: US 8,475,533 B1
Castro  (45) Date of Patent: Jul. 2, 2013

(54) SYSTEM AND STABILIZER FOR SPINAL IMPLANT AND METHODS OF ASSISTING STABILIZATION OF SPINAL IMPLANT

(71) Applicant: Frank Castro, Louisville, KY (US)

(72) Inventor: Frank Castro, Louisville, KY (US)

(73) Assignee: IGIP, LLC, Louisville, KY (US)

(*) Notice: Subject to any disclaimer, the term of this patent is extended or adjusted under 35 U.S.C. 154(b) by 0 days.

(21) Appl. No.: 13/628,107

(22) Filed: Sep. 27, 2012

(51) Int. Cl.
A61F 2/44 (2006.01)

(52) U.S. Cl.
USPC ........................... 623/17.16; 623/17.11

(58) Field of Classification Search
USPC ................. 606/246–249; 623/17.11–17.16
See application file for complete search history.

(56) References Cited

U.S. PATENT DOCUMENTS

| | | | |
|---|---|---|---|
| 5,683,394 A | 11/1997 | Rinner | |
| 6,090,143 A | 7/2000 | Meriwether et al. | |
| 6,231,610 B1 | 5/2001 | Geisler | |
| 6,432,106 B1 | 8/2002 | Fraser | |
| 6,572,619 B2 | 6/2003 | Santilli | |
| 6,770,096 B2 * | 8/2004 | Bolger et al. | 623/17.16 |
| 6,926,737 B2 | 8/2005 | Jackson | |
| 7,182,782 B2 * | 2/2007 | Kirschman | 623/17.11 |
| 7,435,261 B1 | 10/2008 | Castro | |
| 7,942,932 B2 | 5/2011 | Castro | |
| 8,002,832 B2 | 8/2011 | Castro | |
| 8,016,887 B1 | 9/2011 | Castro | |
| 8,075,620 B1 | 12/2011 | Castro | |
| 8,167,945 B1 | 5/2012 | Castro | |
| 8,226,718 B2 | 7/2012 | Castro | |
| 2005/0159813 A1 * | 7/2005 | Molz | 623/17.11 |
| 2010/0305701 A1 | 12/2010 | Castro | |
| 2010/0324681 A1 | 12/2010 | Castro | |
| 2010/0324682 A1 | 12/2010 | Castro | |
| 2012/0004730 A1 | 1/2012 | Castro | |

FOREIGN PATENT DOCUMENTS

| | | |
|---|---|---|
| EP | 2470081 A1 | 7/2012 |
| WO | WO2011/028236 | 3/2011 |
| WO | WO2012/060877 | 5/2012 |

* cited by examiner

*Primary Examiner* — Eduardo C Robert
*Assistant Examiner* — Christina Negrellirodriguez
(74) *Attorney, Agent, or Firm* — Kenneth F. Pearce (57) ABSTRACT

A system, stabilizer and method for assisting the inhibition of the inward advancement of the surgically implanted spinal implant. The current system, stabilizer and method are particularly useful with spinal cages or other implants having one or more apertures about their perimeters.

18 Claims, 7 Drawing Sheets

Positioning a locker proximate an inward side of one of
the spinal implant's plurality of apertures Using a torsion fastener comprising a head capable of movement independent of a direction of
rotation of the torsion fastener's shaft to engage the aperture and the locker, wherein the head
comprises a length greater than a distance between sides of
the surgically created cavity Turning the torsion fastener without locking the head and the locker Rotating the length where the length extends beyond the distance such that the length
inhibits inward advancement of the spinal implant Locking the head, the locker and the torsion fastener

FIG 9

Supplying a locker comprising an arm extending away from the locker and positioning the locker
proximate an inward side of one of the spinal implant's plurality of apertures Using a torsion fastener comprising a head capable of movement independent of a direction of
rotation of the torsion fastener's shaft to engage the aperture and the locker, wherein the head
comprises a length greater than a distance between sides of
the surgically created cavity Turning the torsion fastener without locking the head and the locker Connecting the arm to one of the spinal implant's plurality of apertures for impeding rotation of
the locked locker Rotating the length where the length extends beyond the distance such that the length
inhibits inward advancement of the spinal implant Locking the head, the locker and the torsion fastener

SYSTEM AND STABILIZER FOR SPINAL IMPLANT AND METHODS OF ASSISTING STABILIZATION OF SPINAL IMPLANT

BACKGROUND OF THE INVENTION

1. Field of the Invention

Among other things, the present invention is related to a system, stabilizer and method for a spinal implant. Preferred embodiments of the current invention utilize a plate or a head with a length greater than distance between sides of the surgically created cavity to assist with the inhibition of the inward advancement of the spinal implant after implantation of the spinal implant. Select preferred embodiments provide a nut with an arm extending away from the nut.

2. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) US Published Patent 20050159813-Molz, IV discloses a spinal implant and method for implantation. Paragraph 12 of Molz reads, "The elongate plate 26 also defines a pair of passages 37, 38 that are radially offset from and located on diametrically opposite sides of the longitudinal axis 18. The passages 37, 38 are sized and positioned so as to receive the respective posts 23, 24 extending from the cage 17 therein. As should be appreciated, the angular orientation of the posts 23, 24 extending from the cage 17 is initially offset 90° from the angular orientation of the passages 37, 38 in the plate 26 when the cage 17 is positioned in the first operational configuration illustrated in FIGS. 1 and 2. However, when the cage 17 is rotated to the second operational configuration illustrated in FIGS. 3 and 4, the posts 23, 24 are aligned with the passages 37, 38. Once rotated to the second operational configuration, tightening of the fastener 27 into the threaded opening 22 in the cage 17 results in displacement of the cage 17 toward the plate 26 and positioning of the posts 23, 24 within the passages 37, 38. However, it should be understood that in another embodiment, tightening of the fastener 27 into the threaded opening 22 in the cage 17 may result in displacement of the plate 26 toward the cage 17 to position the posts 23, 24 within the passages 37, 38.

Among other things, Molz does not appear to disclose a stabilizer with a locker positioned inward of the spinal cage's aperture, a torsion fastener engaging the locker, a hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

2) U.S. Pat. No. 5,683,394-Rinner enables a fusion mass constrainer. replacement. In part, Columns 2 and 3 read, "Referring to FIGS. 1-3, a fusion mass constrainer of the present invention is illustrated. The fusion mass constrainer includes a main body portion 1 that includes a hollow cage assembly 3 having an inner cavity 7. The cage assembly includes a generally cylindrical outer surface 5 that is meant to be arranged with its axis in a generally horizontal plane. The cage assembly has a pair of opposing horizontal platforms 4 of generally rectangular cross section which extend from the cage assembly along its length. The outer surface also includes a pair of openings 6, one above and one below the planes formed by the upper and lower surfaces of the platforms.

Migration of bone graft from the proximal end of the cage is prevented by an end cap 2 which fits over and closes the proximal opening. The end cap includes a cylindrical portion 105 of approximately the same diameter as the cavity of the main body portion. A pair of blades 109 are provided integral to the end cap and extend out from opposite sides of the surface of the cylindrical portion.

The end cap is positioned by orienting the blades horizontally and inserting the cylindrical portion into the cavity of the main body portion. The end cap is then rotated in a clockwise direction approximately 90 degrees as best illustrated in FIG. 2. By rotating the blades in this fashion, the blades are forced into the cancellous bone of the vertebrae above and below the injured disc. Once rotated into place, the vertically oriented blades prevent migration of the fusion mass constrainer from its location between the vertebra." Among other things, Rinner does not appear to disclose a stabilizer with a locker positioned inward of the spinal cage's aperture. It can be argued that Rinner's end cap 2 is either a plate or a torsion fastener, but the structure of the Rinner end cap prevents the end cap from being both a plate and a torsion fastener. It also does not appear that Rinner teaches a stabilizer wherein the torsion fastener is secured only to the spinal cage and the stabilizer and not bone after the stabilizer is locked.

3) U.S. Pat. No. 6,090,143-Meriwether, et al. enables a box cage for intervertebral body fusion. In part, Column 4 reads, "To obviate this problem, in accordance with the present invention, and as illustrated in the exploded view of FIG. 2, there is provided a generally rectangular box-like cage member, indicated generally by numeral 30, having four mutually perpendicular sidewalls 32, 34, 36 and 38 of a predetermined height dimension, allowing insertion between adjacent vertebral bodies using either an anterior, a posterior or a lateral approach. Extending between opposed sidewalls 32 and 36 are a plurality of parallel, spaced-apart rib members 40. The rib members are preferably triangular in shape as illustrated terminating in a ridge line 42.

The opposed side edges 32 and 36 also each include a circular aperture, as at 44 and 46, for receiving therein a locking screw member indicated generally by numeral 48. The locking screw 48 includes a head 50 having a non-circular recess 52 formed inwardly of a face surface thereof for receiving an appropriate screw driver-like tool. The locking screw has a raised thread 54 of a predetermined pitch slightly wider than the thickness dimension of the end walls 32 and 36. The root diameter of the locking screw 48 allows it to be fitted through the aperture 44 and advanced until the tapered end portion 56 thereof passes into the aperture 46 of the sidewall 36. The crest diameter of the locking screw 48 is made greater than the height dimension of the mutually perpendicular sidewalls 32, 34, 36 and 38 of the cage member 30, and, as such, the threads project outwardly beyond the level of the edges of the side walls."

Among other things, Meriwether does not appear to disclose a stabilizer with a locker positioned inward of the spinal cage's aperture, a plate with a length greater than at least one of the distances between sides of the surgically created cavity where the plate has a hole proximate an aperture of the spinal cage, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

4) U.S. Pat. No. 6,231,610-Geisler enables an anterior cervical column support device. In part, Columns 3 and 4 reads, "As shown in FIG. 1, the side view of the anterior cervical column support device 10 shows the rear plate 11 attached to the back surface 15 of the support device 10. It also shows a side surface 12a. Each side surface 12a and 12b has the same shape and size. FIG. 1 also shows a side view of the top load bearing surface 13 and the bottom load bearing surface 14. These surfaces 13 and 14 have the same size and shape and are named differently for the purpose of description only. Each surface 13 and 14 includes serrations 18."

Among other things, Geisler does not appear to disclose a stabilizer with a locker positioned inward of the spinal cage's aperture, a plate with a length greater than at least one of the distances between sides of the surgically created cavity where the plate has a hole proximate an aperture of the spinal cage, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

5) U.S. Pat. No. 6,432,106-Fraser enables an anterior lumbar interbody fusion cage and locking plate. In part, Column 4 reads, "FIG. 8 depicts the fusion cage described above with respect to FIGS. 1, 2 and 3 after it has been implanted. In this view, portions of the vertebral bodies are shown cut-away to illustrate the penetration of the bone screws 58 and 60 into the bodies. It is important to note that screw heads 62 and 64 are flush or sub-flush with the anterior face surface 66 of the fusion cage, thus minimizing the likelihood that major blood vessels running along the spine will be injured."

Among other things, Fraser does not appear to disclose a stabilizer with a locker positioned inward of the spinal cage's aperture, a plate with a length greater than at least one of the distances between sides of the surgically created cavity where the plate has a hole proximate an aperture of the spinal cage, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

6) U.S. Pat. No. 6,572,619-Santilli enables a cage plate for spinal fusion and method of operation. In part, Column 5 reads, "Referring to FIGS. 2-4, anterior views and a side elevation view of the cervical spine are shown. The cage 12 of the cage plate 10 is installed in the same manner as is described in U.S. Pat. No. 5,961,554 at columns 4-5. The description set forth in FIG. 5 describes a step-by-step methodology for installing the complete cage plate 10 in adjacent cervical vertebral bodies. It is to be understood that the length of the plate 14 and the cage 12 can be selected to fuse either two or three vertebrae of any portion of the spine."

Among other things, Santilli does not appear to disclose a stabilizer with a locker positioned inward of the spinal cage's aperture, a plate with a length greater than at least one of the distances between sides of the surgically created cavity where the plate has a hole proximate an aperture of the spinal cage, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

7) U.S. Pat. No. 6,770,096-Bolger, et al. enables an interbody spinal stabilization cage and spinal stabilization method. In part, Column 4 reads, "In a preferred embodiment of the invention, said anchoring means 3 have an overall S shape, as illustrated in FIGS. 1 and 2, and the centre of gravity of the S shape is positioned on the axis A of the actuation means 2, as illustrated in FIG. 3."

Among other things, Bolger does not appear to disclose a stabilizer with a locker positioned inward of the spinal cage's aperture, a plate with a length greater than at least one of the distances between sides of the surgically created cavity and the plate having a hole proximate an aperture of the spinal cage, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

8) U.S. Pat. No. 6,926,737-Jackson enables a spinal fusion apparatus and method. In part, Columns 5 and 6 read, "Each of implants 10 and 11 (best seen in FIG. 11) are elongate and have a central axis A. Each of the implants 10 and 11 also are somewhat annular in shape having a central chamber 20, surrounded by a wall 21 having an outer surface 22. The wall 22 is penetrated by a plurality of ports or windows 26 that are radially positioned and open into the central chamber 20. The outer surface 22 also includes partial threads 27 interspaced at opposite corners with the windows 26.

Each implant 10 and 11 has an enclosed rear end 30 and an anterior or front end 31. The implant front end 31 has a threaded bore 32 that is generally aligned with the axis A and an outer generally planar surface 33. When installed, bone chips 35, normally harvested from another part of the body such as the hip, are inserted in the chamber 20 (see FIG. 8).

The plate 12 is relatively rigid, but has a slight amount of resiliency. The plate 12 joins two spaced end caps 15 and 16 having loops 40 and 41 respectively joined by a connector 42. The end caps 15 and 16 are sized and shaped to generally sit snugly against the front end surface 33 of each of the implants 10 and 11 so as to be located at least partially directly anterior of a respective implant 10 and 11. The interior of each illustrated loop 40 and 41 is somewhat oblong. The oblong nature of the loops 40 and 41 is necessary in some cases to allow for various spacing of the implants 10 and 11 and more importantly to allow the second of the set screws 13 or 14 to be started into the associated bore 32. It is foreseen that in certain embodiments the loops 40 and 41 would not be required to be oblong, but could be circular or the like."

Among other things, Jackson does not appear to disclose a stabilizer with a locker positioned inward of the spinal cage's aperture, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer after the stabilizer is locked.

9) U.S. Pat. No. 7,182,782-Kirschman enables a spinal fusion system and method for fusing spinal bones. In part, Column 4 reads, "As illustrated in FIG. 11, the housing 32 is generally U-shaped as shown. In the embodiment being described, the housing 32 comprises a well 33 defining multiple sides and comprising a predetermined shape selected to cause the graft material to be formed into a multi-sided fused coupling between adjacent spinal bones, such as bones 10 and 12 in FIG. 3. Although not shown, the housing 32 could define a shape other than rectangular, such as semi-circular, oval or other suitable shape as may be desired. Note that the housing 32 comprises a first wall 32a, a second wall 32b and a third wall 32c joining the first wall 32a and the second wall 32b. One or more of the walls 32a-32c may comprise a plurality of holes or apertures 40 which facilitate the fusing process. The apertures 40 also permit visualization of graft material 30 on x-rays."

Among other things, Kirschman does not appear to disclose a stabilizer with a locker positioned inward of the spinal cage's aperture, a plate with a length greater than at least one of the distances between sides of the surgically created cavity where the plate has a hole proximate an aperture of the spinal cage, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

10) The assignee of the following: U.S. Pat. No. 7,435,261-Castro enabling a spinal implant and method of using spinal implant, U.S. Pat. No. 7,942,932-Castro enabling a spinal implant and method of using spinal implant, U.S. Pat. No. 8,002,832-Castro enabling a spinal implant and method of using spinal implant, U.S. Pat. No. 8,016,887-Castro enabling a spinal implant with overlay, U.S. Pat. No. 8,075,620-Castro enabling a doughnut-like spinal implant, U.S. Pat. No. 8,167,945-Castro enabling a doughnut-like spinal implant, U.S. Pat. No. 8,226,718-Castro enabling a spinal implant and method of using spinal implant, U.S. Pat. No. 8,246,682-Castro enabling a spinal implant, US Published Patent Application 20120004730-Castro enabling an end cap and connector for a spinal implant, US Published Patent Application 20100305701-Castro enabling a spinal implant, US Published Patent Application 20100324682-Castro enabling a spinal implant, US Published Patent Application 20100324681-Castro enabling a wedge-like spinal implant, European Patent Application 2470081A1 enabling a spinal implant, WIPO Patent Application WO2011/028236 enabling a spinal implant and WIPO Patent Application WO2012/060877 enabling stabilizers, end cap and connector for assisting stabilization of a spinal implant is also the assignee of the current Application for Letters Patent entitled system and stabilizer for spinal implant and methods of assisting stabilization of spinal implant.

Among other things, the above identified Castro references do not appear to disclose a stabilizer with a locker positioned inward of the spinal cage's aperture, a plate with a length greater than at least one of the distances between sides of the surgically created cavity where the plate has a hole proximate an aperture of the spinal cage, a torsion fastener for engaging the locker, the hole of the stabilizer's plate and the spinal cage's aperture, moving or rotating the plate prior to locking the stabilizer for inhibiting the inward advancement of the spinal cage, wherein the torsion fastener is secured only to the spinal cage and the stabilizer and not bone after the stabilizer is locked.

SUMMARY OF THE INVENTION

The present invention provides a system, stabilizer and method capable of assisting the inhibition of the inward advancement of the spinal implant inserted into a surgically created cavity. Preferred embodiments of the current stabilizer can be functional for the stabilizer's intended purpose without the stabilizer's fastener being fastened to bone. In select preferred embodiments, the stabilizer's locker can be provided with an arm that extends away from the locker.

An aspect of a preferred embodiment of the present invention is to provide a novel and nonobvious stabilizer for assisting the stabilization of a spinal implant.

Still another aspect of a preferred embodiment of the present invention is to provide embodiments of a stabilizer including a plate, a nut and a fastener.

It is another aspect of a preferred embodiment of the present invention to provide a stabilizer including a torsion fastener having a head capable of movement independent of the direction of rotation of the torsion fastener's shaft.

Yet another aspect of preferred embodiments the present invention is to provide stabilizers functional with a plethora of spinal implants, such as, including but not limited to, cylindrical-like, cylindrical or box-like cages.

An embodiment of the present invention can be described as a system for assisting the stabilization of a cylindrical spinal cage capable of implantation into a surgically created cavity, wherein the cylindrical spinal cage comprises: a) a first generally open end proximate a cephalic end of the surgically created cavity; b) a second generally open end proximate a caudal end of the surgically created cavity and opposite the first generally open end; and c) a plurality of apertures positioned about the cylindrical spinal cage, wherein at least one of the apertures is a receptacle; the system comprising: I) a stabilizer comprising: a) a nut proximate an inward side of the receptacle; the nut further comprising an arm extending away from the nut and capable of engaging one of the plurality of apertures; b) a plate comprising a length greater than at least one of a plurality of distances between pairs of opposing sides of the surgically created cavity, wherein the plate comprises a hole proximate an outward side of the receptacle; and c) a torsion fastener engaging the hole, the receptacle and the nut attaching the nut and the plate to the spinal cylindrical cage, wherein prior to locking the stabilizer with a combination comprising the torsion fastener, the plate and the nut, the length is rotatable to a position extending beyond one of the pairs of opposing sides for inhibiting inward advancement of the spinal cylindrical cage, and wherein the torsion fastener is secured only to the spinal cylindrical cage and the stabilizer; and II) a tool capable of extending into the spinal cylindrical cage and holding the nut proximate the inward side of the receptacle until the tool is removed from the spinal cylindrical cage.

Another embodiment of the present invention can be described as a method for inhibiting inward movement of a spinal implant including a plurality of apertures, wherein the spinal implant is capable of implantation into a surgically created cavity; the method comprising the steps of: a) positioning a locker proximate an inward side of one of the plurality of apertures; b) positioning a hole of a plate proximate an outward side of the one of said plurality of apertures, wherein the plate has a length greater than at least one of a plurality of distances between pairs of opposing sides of the surgically created cavity; c) using a torsion fastener to engage the hole, the one of said plurality of apertures and the locker; d) turning the torsion fastener without locking a combination comprising the torsion fastener, the plate and the locker; e) prior to locking the combination, rotating the length where the length extends beyond one of the plurality of distances such that the length inhibits inward advancement of the spinal implant; and f) locking the combination such that the torsion fastener is secured only to the spinal implant and the stabilizer.

Yet another embodiment of the present invention can be described as a system for stabilizing a cylindrical spinal cage capable of implantation into a surgically created cavity, wherein the cylindrical spinal cage comprises: a) a first generally open end proximate a cephalic end of the surgically created cavity; b) a second generally open end proximate a caudal end of the surgically created cavity and opposite the first generally open end; and c) a plurality of apertures positioned about the cylindrical spinal cage, wherein at least one of the apertures is a receptacle; said system comprising: I) a stabilizer comprising: a) a locker proximate an inward side of the receptacle; b) a torsion fastener comprising a head capable of movement independent of a direction of rotation of the torsion fastener's shaft; the head comprising a length greater than at least one of a plurality of distances between pairs of opposing sides of the surgically created cavity, wherein the torsion fastener engages the receptacle and the locker when locked, and prior to locking the stabilizer, the head is moved such that the length extends beyond one of the pairs of opposing sides for inhibiting inward advancement of the spinal cylindrical cage; and II) a tool capable of extending into the spinal cylindrical cage and holding the locker proximate the inward side of the receptacle until the tool is removed from the spinal cylindrical cage.

In still another embodiment, the present invention can be described as a stabilizer for a spinal implant implantable into a surgically created cavity, wherein the spinal implant comprises a cephalic end, a caudal end and one or more apertures positioned about the spinal implant, wherein at least one of said ends is capable of receiving a tool; the stabilizer comprising: a) a locker locatable within the spinal implant; b) a plate comprising a hole and a length greater than a distance between opposing sides of the surgically created cavity; and c) a fastener engaging the hole, one of the apertures and the locker, wherein prior to locking the stabilizer with a combination comprising the fastener, the plate and the locker, the length is movable to a position extending beyond the distance for inhibiting inward advancement of the spinal implant, and wherein the fastener is secured only to the spinal implant and the stabilizer.

Another embodiment of the present invention can be described as a method for inhibiting inward movement of a spinal implant including one or more apertures, wherein the spinal implant is capable of implantation into a surgically created cavity; the method comprising the steps of: a) positioning a locker proximate an inward side of one of the apertures; b) using a torsion fastener comprising a head capable of movement independent of a direction of rotation of the torsion fastener's shaft to engage the aperture and the locker, wherein the head comprises a length greater than a distance between opposing sides of the surgically created cavity; c) turning the torsion fastener without locking a combination comprising the torsion fastener, the head and the locker; d) prior to locking the combination, rotating the length where the length extends beyond the distance such that the length inhibits inward advancement of the spinal implant; and e) locking the combination.

Yet another embodiment of the present invention can be described as a stabilizer for a spinal implant implantable into a surgically created cavity, wherein the spinal implant comprises a cephalic end, a caudal end and one or more apertures positioned about the spinal implant; the stabilizer comprising: a) a locker locatable within the spinal implant; and b) a fastener capable of engaging one of the apertures and the locker, wherein the fastener comprises: i) an inward section engaging the locker; and ii) an outward section comprising a length greater than a distance between two sides of the surgically created cavity, wherein prior to locking the stabilizer, the length is positioned to extend beyond the distance for inhibiting inward advancement of the spinal implant.

It is the novel and unique interaction of these simple elements which creates the system, apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

The practice of the present invention requires the removal of mammalian tissue to create a cavity for receiving a spinal implant. Depending on the surgical procedure performed, spinal implants of varying sizes and shapes may be selected for eventual implantation into the surgical cavity. Preferred embodiments of the current stabilizer are manufactured in differing sizes and shapes and are compatible with numerous spinal implants or cages.

In the most general sense, the current invention is a system and stabilizer for assisting with the stabilization of a spinal implant implantable into the surgically created cavity. Stabilizers in accord with the present invention can have plates, lockers or nuts, torsion or other fasteners and/or a torsion fastener with a head capable of movement independent of the direction of rotation of the torsion fastener. Prior to locking the stabilizer to the spinal cage, the plate or head is rotated or moved such that the length of the plate or head extends beyond a pair of sides of the surgically created cavity. A locked stabilizer assists with the inhibition of the inward advancement of the spinal implant toward the spinal cord. Select preferred embodiments of the stabilizer's locker or nut are provided with an arm capable of interlocking with an aperture of the spinal cage.

Stabilizers of the current invention can be manufactured of biocompatible metals, plastics or combinations thereof, and preferred embodiments are manufactured of titanium, titanium alloys, stainless steel, non-resorbable and resorbable polymers. The current system and stabilizer meet the long felt but unfilled needs of providing a simple stabilizer capable of inhibiting inward advancement of the spinal implant. Further, the current stabilizer does not require that the fastener be secured to bone for functionality.

Figure 1:
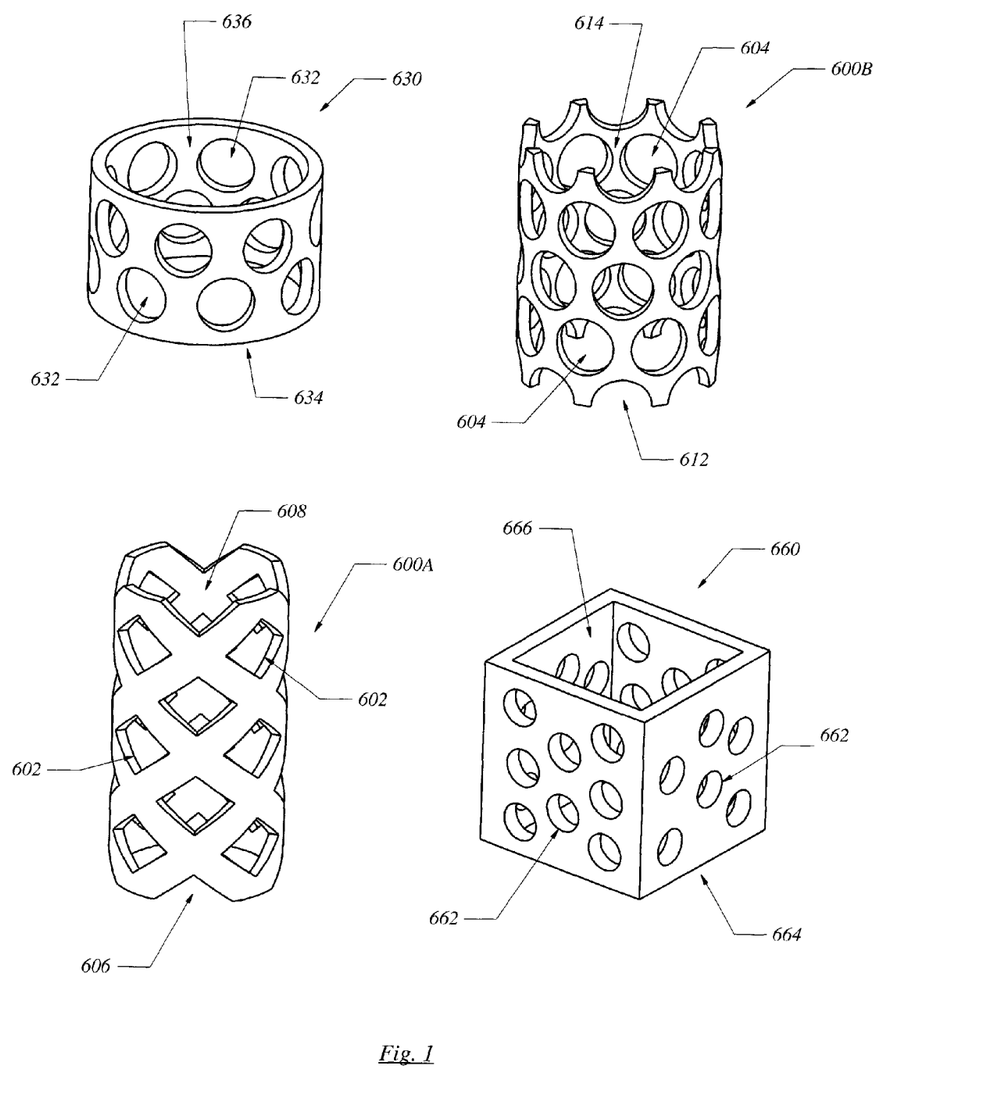
FIG. 1 is a perspective exemplifying some of the kinds of cages or spinal implants compatible for use with the current system, stabilizer and methods.

Embodiments portrayed in FIG. 1 exemplify types of cages or spinal implants compatible for use with the current system, stabilizer and methods, e.g., cylindrical-like (600A and 600B), cylindrical (630) and box-like (660) cages. As shown in FIG. 1, all spinal implants (600A, 600B, 630 and 660) are provided with at least one aperture (602, 604, 632 or 662) positioned about a perimeter of the cage and at least one generally open end (606, 608, 612, 614, 634, 636, 664 or 666). For most embodiments of the spinal implants associated with the current invention, the cages are provided with a plurality of apertures (602, 604, 632 and 662) about the perimeter of the spinal implant. When implanted into a surgically created cavity about the spinal region of mammals, cages (600A, 600B, 630 or 660) have opposing cephalic end caudal ends.

Figure 2:
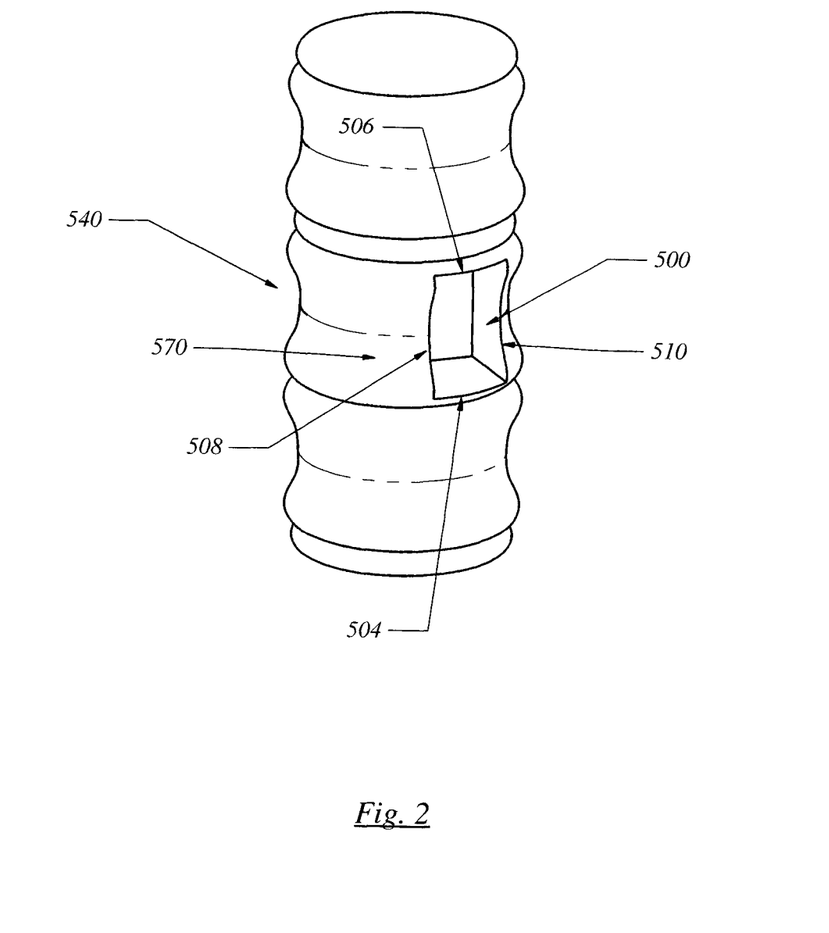
FIG. 2 is perspective of a length of mammalian spine (540) with a surgically created cavity (500) in a section of the mammalian spine (540).

FIG. 2 is perspective of a length of mammalian spine (540) with a surgically created cavity (500) in a section of the mammalian spine (540). As shown in FIG. 2, surgically created cavity (500) is generally rectangular and has opposing sides (504 and 506) and (508 and 510). However, when surgically parameters require, the surgically created cavity may be of any shape acceptable in the art and the shape of perimeter of the surgically created cavity is immaterial to the practice of the present invention.

Figure 3:
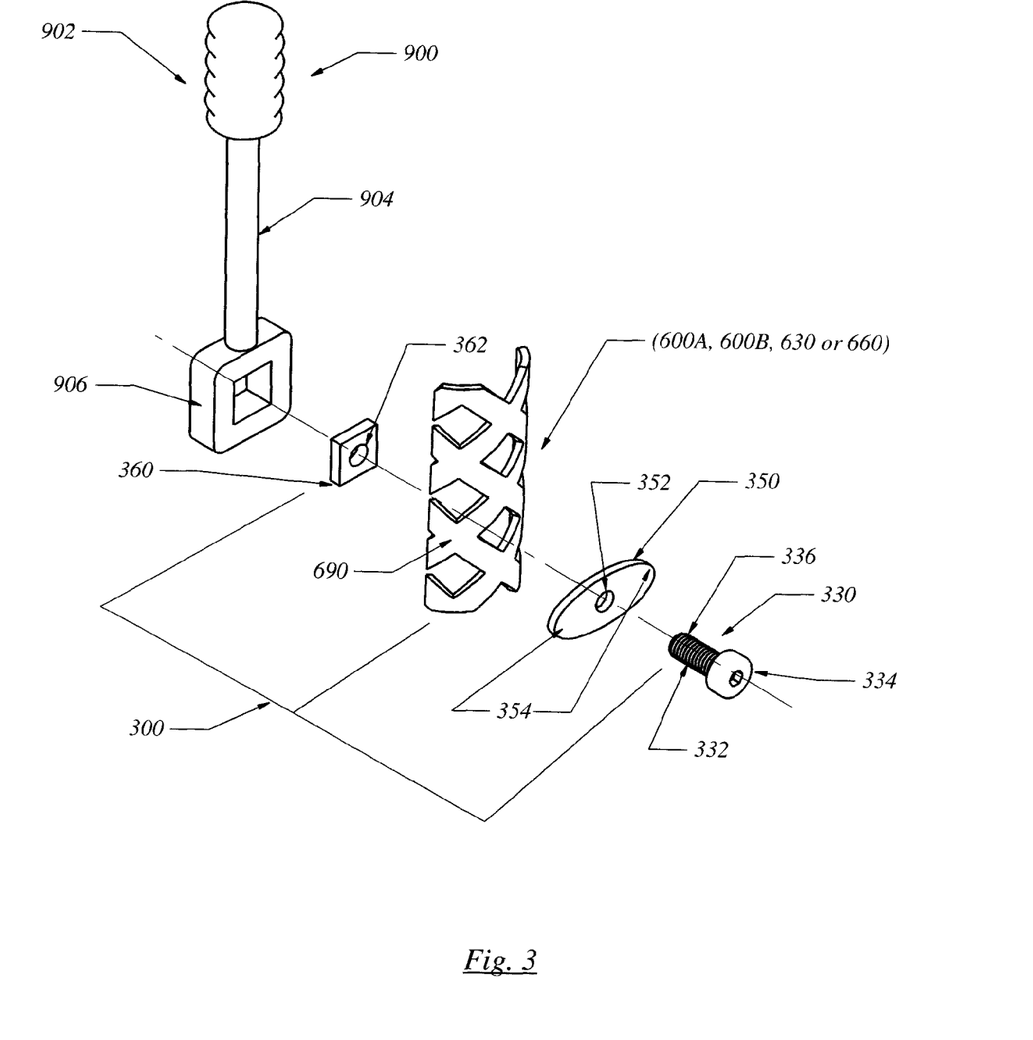
FIG. 3 is an exploded view of section (690) of cage (600A, 600B, 630 or 660) and a preferred embodiment of the current system of the present invention and a tool (900) utilizable in the practice of the present invention.

FIG. 3 is an exploded view of a representative section (690) of cage (600A, 600B, 630 or 660) and a preferred embodiment of the current system of the present invention. As shown, a preferred embodiment of a system of the present invention includes a tool (900) and a stabilizer (300).

A select preferred embodiment of stabilizer (300) includes a torsion fastener (330), plate (350) and nut or locker (360). Torsion fastener (330) can be a screw, bolt or other fastener that is provided with threads (332), shaft (336) and head (334). Although not shown in FIG. 3, other kinds of fasteners compatible the present invention include but are not limited to welded or expansion fasteners. Plate (350) is provided with hole (352) and has a length (354) that is greater than a distance between two sides of the surgically created cavity (500) into which the spinal cage (600A, 600B, 630 or 660) is to be implanted. Depending on surgical parameters, plate (350) can be straight or contoured. Nut (360) includes threaded aperture (362) for engaging threads (332) of shaft (336) of torsion fastener (330). For select preferred embodiments utilizing an expansion or a welded fastener, locker (360) can be any device acceptable in the art.

Tool (900) includes handle (902), shaft (904) and holder (906) for holding locker (360) proximate an inward side of receptacle or aperture (602, 604, 632 or 662) of spinal cage (600A, 600B, 630 or 660) until tool (900) is taken away from spinal implant (600A, 600B, 630 or 660). Within the scope of the present invention, as required by surgical parameters, specialized tool (900) is shaped and manufactured in acceptable dimensions for fitting inside the spinal implant to hold locker (360) proximate receptacle (602, 604, 632 or 662).

In the practice of a preferred embodiment of the current invention, locker (360) is positioned proximate an inward side of aperture (602, 604, 632 or 662) of cage (600A, 600B, 630 or 660). Hole (352) of plate (350) is positioned opposite locker (360) and proximate an outward side of aperture (602, 604, 632 or 662) of cage (600A, 600B, 630 or 660). Torsion fastener (330) secures plate (350) and nut (360) against section (690) of spinal implant (600A, 600B, 630 or 660). Prior to locking stabilizer (300) against section (690), length (354) of plate (350) is positioned or rotated where length (354) extends beyond one of the plurality of distances between sides of the surgical cavity such that length (354) inhibits inward advancement of the spinal implant (600A, 600B, 630 or 660).

Figure 4:
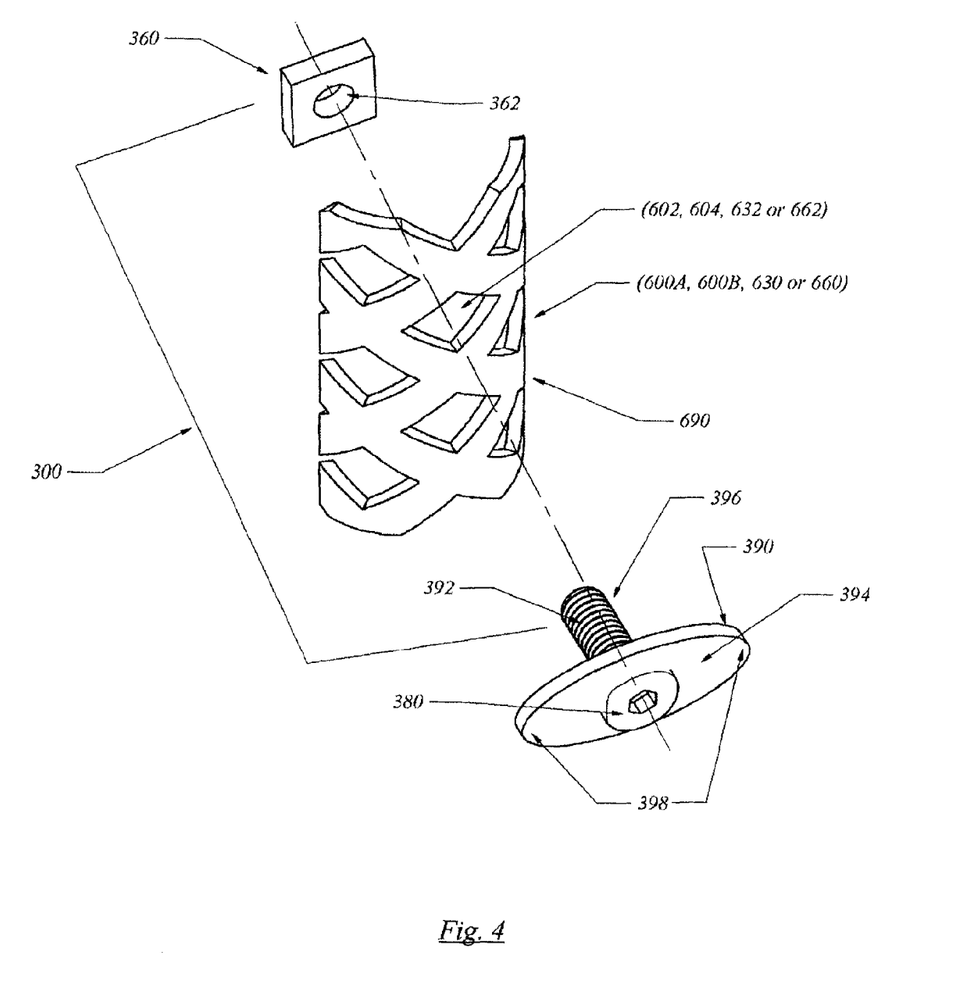
FIG. 4 is an exploded view of section (690) of cage (600A, 600B, 630 or 660) and a preferred embodiment of the current system of the present invention.

FIG. 4 is an exploded view of a representative section (690) of cage (600A, 600B, 630 or 660) and a preferred embodiment of the current system of the present invention. A select preferred embodiment of stabilizer (300) includes a torsion fastener (390) and nut or locker (360). Torsion fastener (390) can be a screw, bolt or other fastener that is provided with threads (392), shaft (396) and head (394). Head (394) is capable of movement independent of a direction of rotation of shaft (396). Outward end (380) of shaft (396) is provided with face capable of interlocking with torsion generating tool (not shown). Head (394) also includes a length (398) that is greater than a distance between two sides of the surgically created cavity (500) into which the spinal cage (600A, 600B, 630 or 660) is to be implanted. Depending on surgical parameters, head (394) can be straight or contoured. Nut (360) includes threaded aperture (362) for engaging threads (392) of shaft (396) of torsion fastener (390).

In the practice of a preferred embodiment of the current invention, locker (360) is positioned proximate an inward side of aperture (602, 604, 632 or 662) of cage (600A, 600B, 630 or 660). Torsion fastener (390) secures head (394) and nut (360) against section (690) of spinal implant (600A, 600B, 630 or 660). Prior to locking stabilizer (300) against section (690), length (398) of head (394) is positioned where length (398) extends beyond one of the plurality of distances between sides of the surgical cavity such that length (398) inhibits inward advancement of the spinal implant (600A, 600B, 630 or 660).

Figure 5:
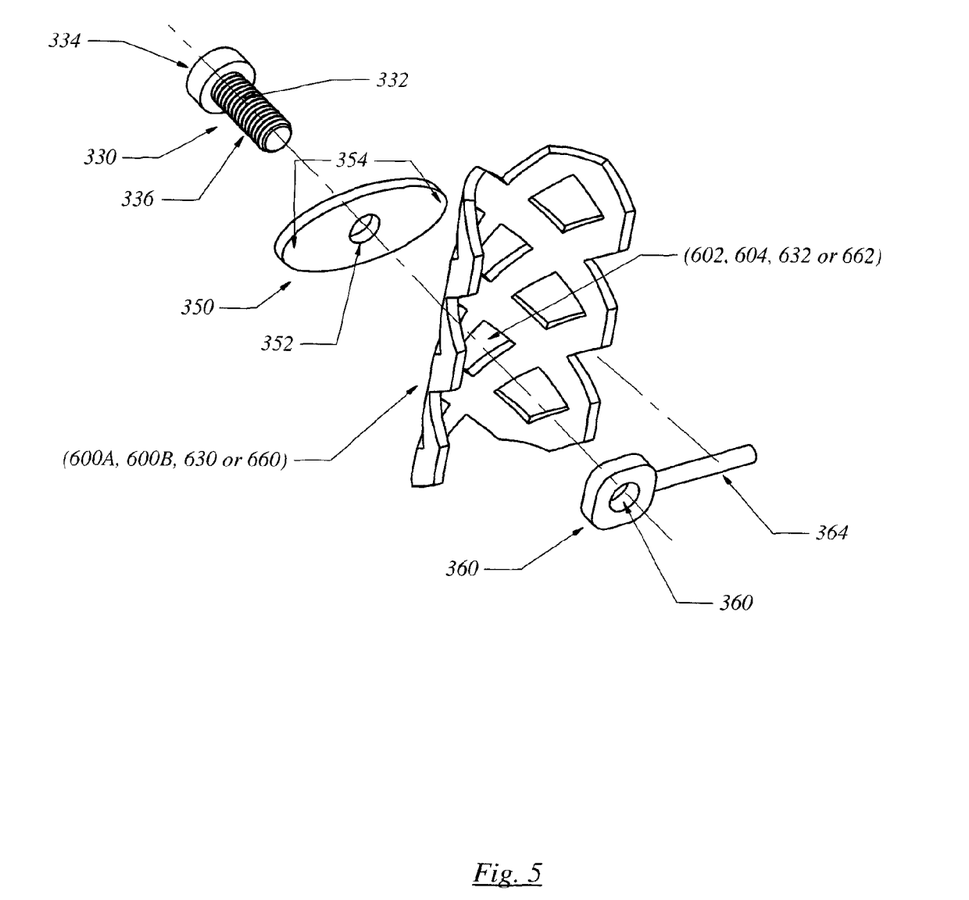
FIG. 5 is an exploded view of cage (600A, 600B, 630 or 660) and a preferred embodiment of the current system of the present invention.
Figure 6:
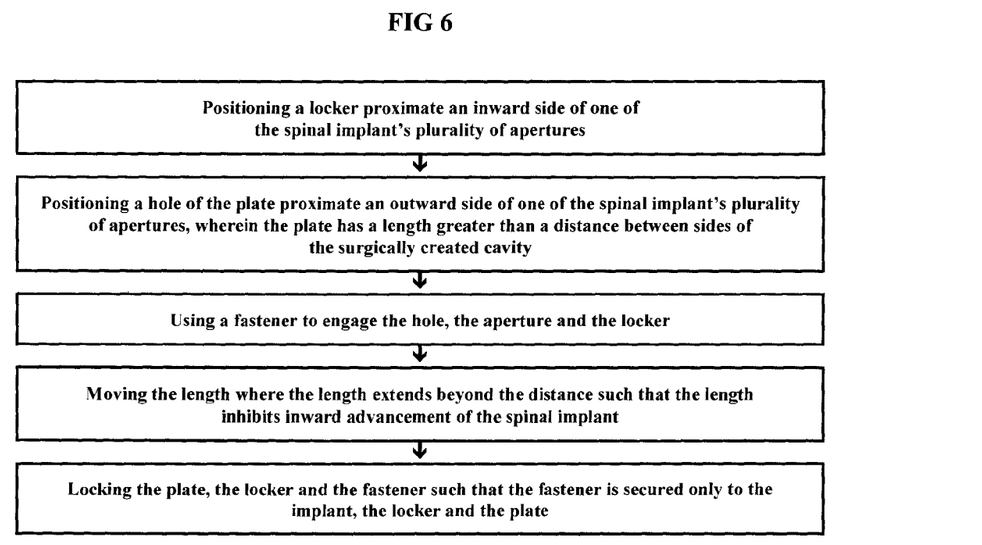
FIG. 6 is an exemplification of the steps of a preferred embodiment of the current system and method.
Figure 7:
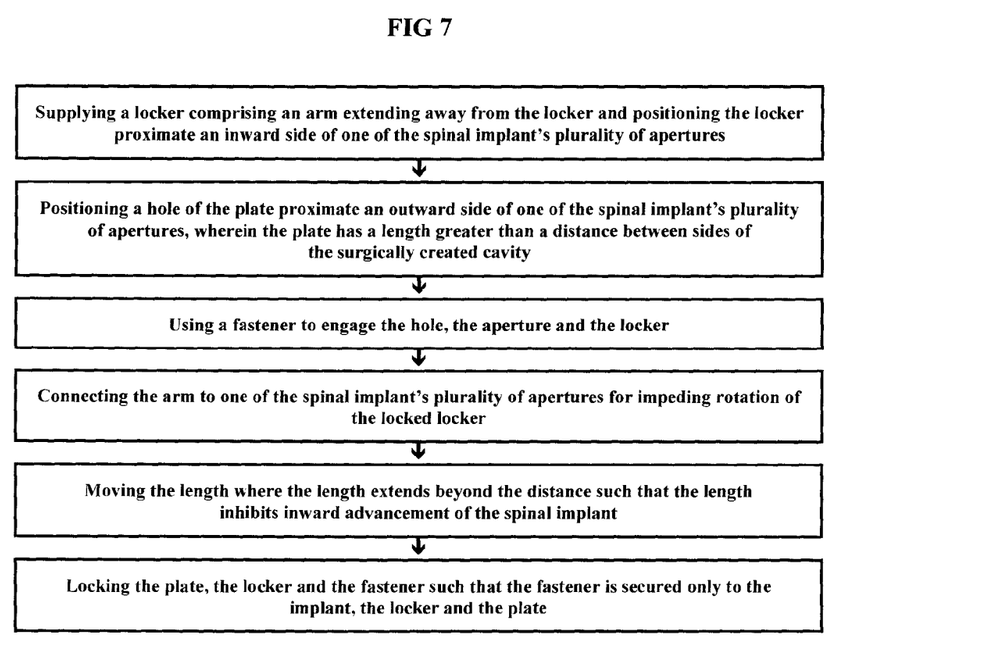
FIG. 7 is a diagrammatic representation of the steps of a preferred embodiment of the current system and method.
Figure 8:
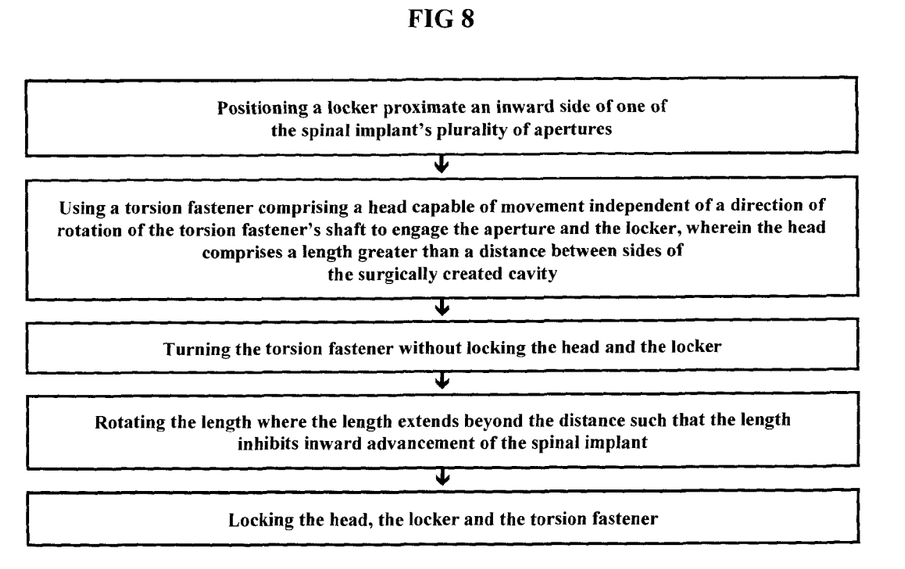
FIG. 8 is a diagrammatic representation of the steps of a preferred embodiment of the current system and method.
Figure 9:
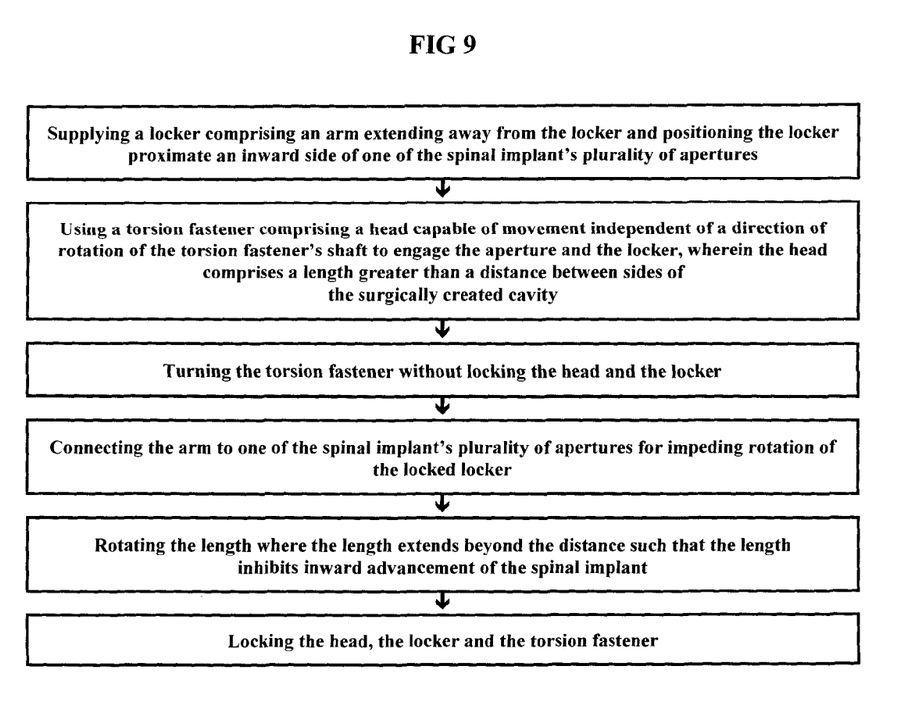
FIG. 9 is an exemplification of the steps of a preferred embodiment of the current system and method.

FIG. 5 is an exploded view of a representative section of cage (600A, 600B, 630 or 660) and a preferred embodiment of the current system of the present invention. A select preferred embodiment of stabilizer (300) includes a torsion fastener (330), plate (350) and nut or locker (360). Torsion fastener (330) can be a screw, bolt or other fastener that is provided with threads (332), shaft (336) and head (334). Plate (350) is provided with hole (352) and has a length (354) that is greater than a distance between two sides of the surgically created cavity (500) into which the spinal cage (600A, 600B, 630 or 660) is to be implanted. Depending on surgical parameters, plate (350) can be straight or contoured. Nut (360) includes threaded aperture (362) for engaging threads (332) of shaft (336) of torsion fastener (330). In select preferred embodiments, locker (360) can be provided with arm (364).

In the practice of a preferred embodiment of the current invention, locker (360) is positioned proximate an inward side of aperture (602, 604, 632 or 662) of cage (600A, 600B, 630 or 660). Hole (352) of plate (350) is positioned opposite locker (360) and proximate an outward side of aperture (602, 604, 632 or 662) of cage (600A, 600B, 630 or 660). Torsion fastener (330) secures plate (350) and nut (360) against spinal implant (600A, 600B, 630 or 660). Prior to locking stabilizer (300) against the spinal implant, arm (364) of locker (360) is positioned to engage one of the apertures (602, 604, 632 or 662) other than the aperture engaged by torsion fastener (330) and length (354) of plate (350). Prior to locking stabilizer (300), plate (350) is positioned or rotated where length (354) extends beyond one of the plurality of distances between sides of the surgical cavity (500) such that length (354) inhibits inward advancement of the spinal implant (600A, 600B, 630 or 660). Interlocking arm (364) with one of the apertures (602, 604, 632 or 662) of spinal implant (600A, 600B, 630 or 660) other than the aperture engaged by torsion fastener (330) can further inhibit any potential rotation of locker (360) after the locking of stabilizer (300). In select preferred embodiments, arm (364) can be manufactured such that arm (364) can be flexed by the surgeon prior to engagement of an aperture (602, 604, 632 or 662) and returns to an inflexible state after arm (364) is interlocked with one of the apertures (602, 604, 632 or 662) of spinal implant (600A, 600B, 630 or 660).

Steps associated with the practice of the methods of preferred embodiments the present invention are set forth in FIGS. 6-9. Those steps are related to the practice of using the stabilizer structures previously set forth.

Having disclosed the invention as required by Title 35 of the United States Code, Applicant now prays respectfully that Letters Patent be granted for his invention in accordance with the scope of the claims appended hereto.

What is claimed is:

1. A system for assisting the stabilization of a cylindrical spinal cage capable of implantation into a surgically created cavity, wherein said cylindrical spinal cage comprises:
   a) a first generally open end proximate a cephalic end of said surgically created cavity;
   b) a second generally open end proximate a caudal end of said surgically created cavity and opposite said first generally open end; and
   c) a plurality of apertures positioned about said cylindrical spinal cage, wherein at least one of said apertures is a receptacle;
   said system comprising:
   I) a stabilizer comprising:
   a) a nut proximate an inward side of said receptacle; said nut further comprising an arm extending away from said nut and capable of engaging one of said plurality of apertures;
   b) a plate comprising a length greater than at least one of a plurality of distances between pairs of opposing sides of said surgically created cavity, wherein said plate comprises a hole proximate an outward side of said receptacle; and
   c) a torsion fastener engaging said hole, said receptacle and said nut; said torsion fastener attaching said nut and said plate to said spinal cylindrical cage, wherein prior to locking said stabilizer with a combination comprising said torsion fastener, said plate and said nut, said length is rotatable to a position extending beyond one of said pairs of opposing sides for inhibiting inward advancement of said spinal cylindrical cage, and wherein said torsion fastener is secured only to said spinal cylindrical cage and said stabilizer; and
   II) a tool capable of extending into said spinal cylindrical cage and holding said nut proximate said inward side of said receptacle until said tool is removed from said spinal cylindrical cage.

2. A method for inhibiting inward movement of a spinal implant including a plurality of apertures, wherein said spinal implant is capable of implantation into a surgically created cavity; said method comprising the steps of:
   a) positioning a locker proximate an inward side of one of said plurality of apertures;
   b) positioning a hole of a plate proximate an outward side of said one of said plurality of apertures, wherein said plate has a length greater than at least one of a plurality of distances between pairs of opposing sides of said surgically created cavity;
   c) using a torsion fastener to engage said hole, said one of said plurality of apertures and said locker;
   d) turning said torsion fastener without locking a combination comprising said torsion fastener, said plate and said locker;
   e) prior to locking said combination, rotating said length where said length extends beyond one of said plurality of distances such that said length inhibits inward advancement of said spinal implant; and
   f) locking said combination such that said torsion fastener is secured only to said spinal implant and said stabilizer.

3. The method of claim 2 further comprising the steps of:
   a) supplying said locker further comprising an arm extending away from said locker; and
   b) connecting said arm to one of said plurality of apertures other than said aperture engaged by said torsion fastener for impeding rotation of said locked locker.

4. A system for stabilizing a cylindrical spinal cage capable of implantation into a surgically created cavity, wherein said cylindrical spinal cage comprises:
   a) a first generally open end proximate a cephalic end of said surgically created cavity;
   b) a second generally open end proximate a caudal end of said surgically created cavity and opposite said first generally open end; and
   c) a plurality of apertures positioned about said cylindrical spinal cage, wherein at least one of said apertures is a receptacle;
   said system comprising:
   I) a stabilizer comprising:
   a) a locker proximate an inward side of said receptacle;
   b) a torsion fastener comprising a head capable of movement independent of a direction of rotation of said torsion fastener's shaft; said head comprising a length greater than at least one of a plurality of distances between pairs of opposing sides of said surgically created cavity, wherein said torsion fastener engages said receptacle and said locker when locked, and prior to locking said stabilizer, said head is moved such that said length extends beyond one of said pairs of opposing sides for inhibiting inward advancement of said spinal cylindrical cage; and
   II) a tool capable of extending into said spinal cylindrical cage and holding said locker proximate said inward side of said receptacle until said tool is removed from said spinal cylindrical cage.

5. The system of claim 4 wherein said locker further comprises an arm connected to one of said plurality of apertures other than said aperture engaged by said torsion fastener.

6. A stabilizer for a spinal implant implantable into a surgically created cavity, wherein said spinal implant comprises a cephalic end, a caudal end and one or more apertures positioned about said spinal implant, wherein at least one of said ends is capable of receiving a tool; said stabilizer comprising:
   a) a locker locatable within said spinal implant;
   b) a plate comprising a hole and a length greater than a distance between opposing sides of said surgically created cavity; and
   c) a fastener engaging said hole, one of said apertures and said locker, wherein prior to locking said stabilizer with a combination comprising said fastener, said plate and said locker, said length is movable to a position extending beyond said distance for inhibiting inward advancement of said spinal implant, and wherein said fastener is secured only to said spinal implant and said stabilizer.

7. The stabilizer of claim 6, wherein said fastener is a torsion fastener.

8. The stabilizer of claim 7, wherein said locker further comprises an arm connected to one of said plurality of apertures other than said aperture engaged by said torsion fastener.

9. A method for inhibiting inward movement of a spinal implant including one or more apertures, wherein said spinal implant is capable of implantation into a surgically created cavity; said method comprising the steps of:
 a) positioning a locker proximate an inward side of one of said apertures;
 b) using a torsion fastener comprising a head capable of movement independent of a direction of rotation of said torsion fastener's shaft to engage said aperture and said locker, wherein said head comprises a length greater than a distance between opposing sides of said surgically created cavity;
 c) turning said torsion fastener without locking a combination comprising said torsion fastener, said head and said locker;
 d) prior to locking said combination, rotating said length where said length extends beyond said distance such that said length inhibits inward advancement of said spinal implant; and
 e) locking said combination.

10. The method of claim 9 further comprising the steps of:
 a) supplying said locker further comprising an arm extending away from said locker; and
 b) connecting said arm to one of said plurality of apertures other than said aperture engaged by said torsion fastener for impeding rotation of said locked locker.

11. The method of claim 10, wherein said torsion fastener is secured only to said spinal implant and said stabilizer.

12. A stabilizer for a spinal implant implantable into a surgically created cavity, wherein said spinal implant comprises a cephalic end, a caudal end and one or more apertures positioned about said spinal implant; said stabilizer comprising:
 a) a locker locatable within said spinal implant; and
 b) a fastener capable of engaging one of said apertures and said locker, wherein said fastener comprises:
  i) an inward section engaging said locker; and
  ii) an outward section comprising a length greater than a distance between two sides of said surgically created cavity, wherein prior to locking said stabilizer, said length is positioned to extend beyond said distance for inhibiting inward advancement of said spinal implant.

13. The stabilizer of claim 12, wherein said fastener is secured only to said spinal implant and said stabilizer.

14. The stabilizer of claim 13, wherein said fastener is a torsion fastener.

15. The stabilizer of claim 13, wherein said fastener further comprises a weld.

16. The stabilizer of claim 13, wherein said fastener is an expansion fastener.

17. The stabilizer of claim 13, wherein said locker further comprises an arm connected to one of said plurality of apertures other than said aperture engaged by said torsion fastener.

18. The stabilizer of claim 17, wherein said fastener is a torsion fastener.

* * * * *